United States Patent
De Lambert et al.

(10) Patent No.: US 8,460,923 B2
(45) Date of Patent: *Jun. 11, 2013

(54) AFFINITY HYDROGEL AND LABEL INDEPENDENT DETECTION METHODS THEREOF

(75) Inventors: Bertrand De Lambert, Senus (FR); David Henry, Morigny-Champigny (FR)

(73) Assignee: Corning Incorporated, Corning, NY (US)

( * ) Notice: Subject to any disclaimer, the term of this patent is extended or adjusted under 35 U.S.C. 154(b) by 107 days.

This patent is subject to a terminal disclaimer.

(21) Appl. No.: 13/033,939

(22) Filed: Feb. 24, 2011

(65) Prior Publication Data

US 2012/0045772 A1 Feb. 23, 2012

(30) Foreign Application Priority Data

Feb. 25, 2010 (EP) .................................. 10305186

(51) Int. Cl.
C12M 1/34 (2006.01)
C12M 1/00 (2006.01)

(52) U.S. Cl.
USPC .................. 435/287.9; 435/283.1; 435/287.1; 435/287.7

(58) Field of Classification Search
None
See application file for complete search history.

(56) References Cited

U.S. PATENT DOCUMENTS

| | | | |
|---|---|---|---|
| 4,887,830 A | 12/1989 | Fought et al. | |
| 5,436,161 A | 7/1995 | Bergstrom et al. | |
| 8,101,405 B2 * | 1/2012 | De Lambert et al. | 435/287.9 |
| 2006/0014232 A1 | 1/2006 | Inagawa et al. | |
| 2010/0159499 A1 * | 6/2010 | Baker et al. | 435/29 |
| 2012/0288939 A1 * | 11/2012 | Baker et al. | 435/396 |

FOREIGN PATENT DOCUMENTS

| | | |
|---|---|---|
| EP | 0226470 | 6/1987 |
| WO | 2004/046724 | 6/2004 |
| WO | 2007/049269 | 5/2007 |

OTHER PUBLICATIONS

Lofas, et al., "A Novel Hydrogel Matrix on Gold Surfaces in Surface Plasmon Resonance Sensors for Fast and Efficient Covalent Mmobilization of Ligands," J. Chem. Soc., Chem. Commun., 1990, 21, 15261528.

Gershon, et al., "Stable Chelating Linkage for Reversible Immobilization of Oligohistidine Tagged Proteins in the Biacore Surface Plasmon Resonance Detector." Journal of Immunological Methods, 1995, vol. 183, pp. 65-76.

Willard, et al., "Covalent Immobilization of Histidinetagged Proteins for Surface Plasmon Resonance," Anal. Biochem., 2006, vol. 353, pp. 147-149.

Wear, et al., "A Surface Plasmon Resonance-Based Assay for Small Molecule Inhibitors of Human Cyclophilin A," Anal. Biochem., 2005, vol. 345, pp. 214226.

Jain, et al., "High Capacity Purification of His-Tagged Proteins by Affinity Membranes Containing Functionalized Polymer Brushes," Biomacromolecules, 2007, 8, pp. 3102-3107.

Yu, et al., "Functional Hydrogel Surfaces: Binding Kinesin Based Molecular Motor Proteins to Selected Patterned Sites," Advanced functional materials, 2005, 15, pp. 1303-1309.

Dai, et al., "High Capacity Binding of Proteins by Poly(Acrylic Acid) Brushes and their Derivatives," Langmuir, 2006, 22, pp. 4274-4281.

Cullen, et al., "Polymeric Brushes As Functional Templates for Immobilizing Ribonuclease A: Study of Binding Kinetics and Activity," Langmuir, 2008, 24, pp. 913-920.

* cited by examiner

*Primary Examiner* — Shafiqul Haq
(74) *Attorney, Agent, or Firm* — John L. Haack

(57) ABSTRACT

A biosensor article including a substrate having polymer modified surface, the polymer comprising the formula (I)

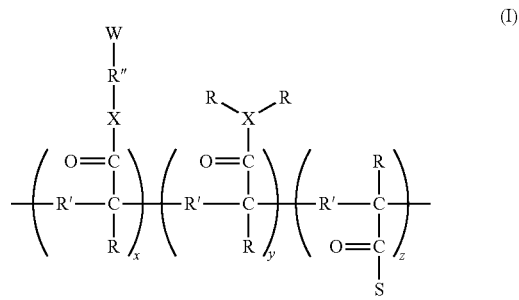

where (x), (y), (z), R, R', R", S, W, and X, are as defined herein. Methods for making the biosensor article or cell culture article, and methods for performing an assay of, for example, a bioentity, a ligand thereof, or both, with the biosensor article are also disclosed.

6 Claims, 9 Drawing Sheets

AFFINITY HYDROGEL AND LABEL INDEPENDENT DETECTION METHODS THEREOF

CLAIMING BENEFIT OF PRIOR FIELD EUROPEAN APPLICATION

This application claims the benefit of priority under 35 U.S.C. §119 of European Patent Application Serial No. EP10305186.8, filed on Feb. 25, 2010. The entire disclosure of publications and patent documents mentioned herein are incorporated by reference.

BACKGROUND

The disclosure generally relates to biosensors for label independent detection (LID), and more particularly to surface chemistry for a high efficiency biosensor, such as Epic® biosensors, and to methods of preparation and use.

SUMMARY

The disclosure provides surface treated biosensor articles for label independent detection (LID), and methods for their preparation and use. The biosensors have high binding efficiency, and like properties, in resonant grating and like sensing applications. The disclosure also concerns systems and methods providing sensors capable of immobilizing bioentities (e.g., receptor proteins, and like cellular targets) at high density and providing superior sensitivity with respect to detecting an analyte. The LID biosensors of the disclosure have surfaces that can provide high sensitivity for the detection of bio-molecular recognition events. The biosensor surfaces of the disclosure can exhibit increased ligand binding, consume less protein, and provide greater sensitivity compared to known biosensor surfaces. The biosensor surfaces of the disclosure are also suitable for cell culture.

BRIEF DESCRIPTION OF THE DRAWINGS

In embodiments of the disclosure.

DETAILED DESCRIPTION

Figure 1A:
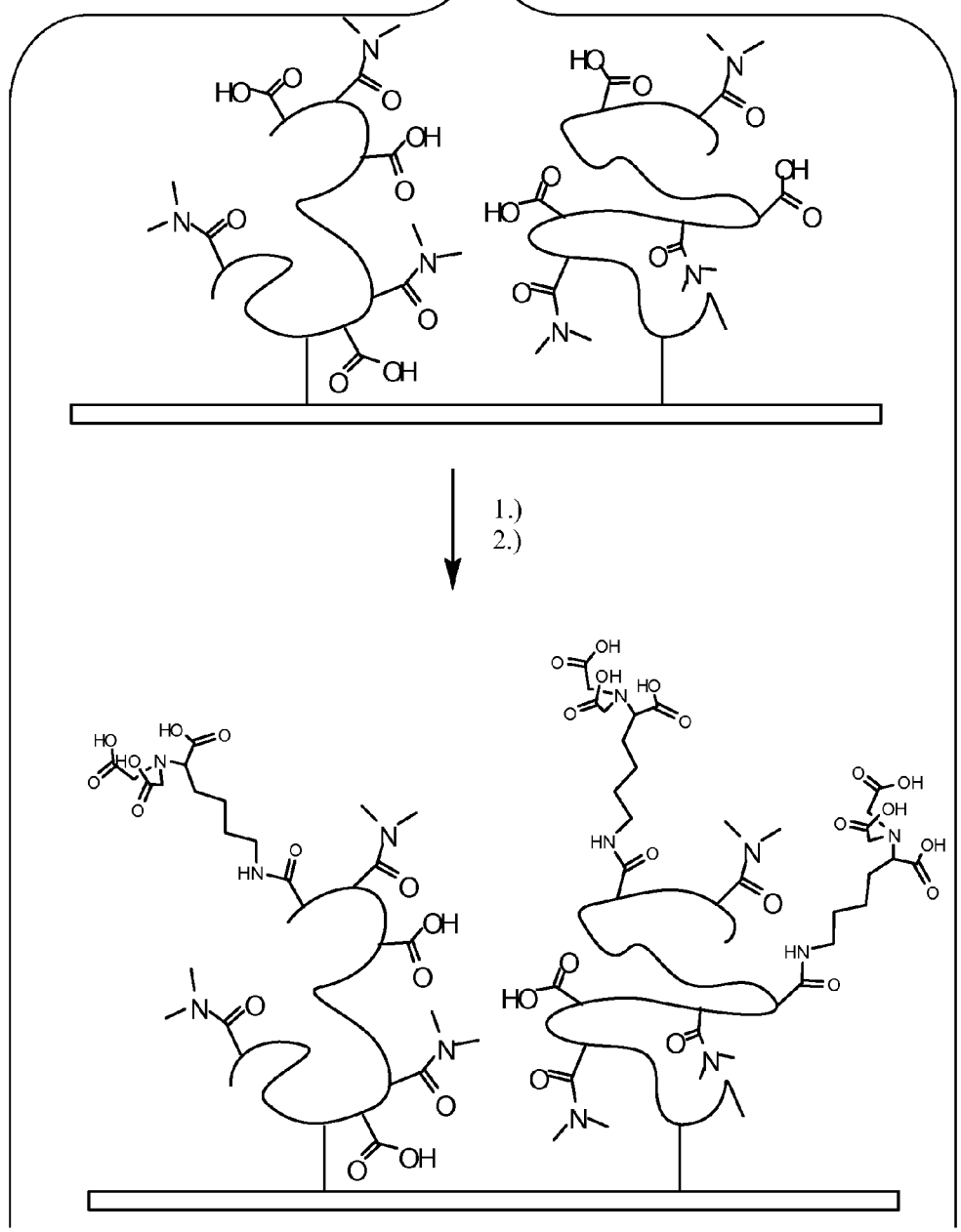
FIG. 1A shows a schematic of a method for preparing the disclosed surface modification.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"Assay," "assaying," or like terms refers to an analysis to determine, for example, the presence, absence, quantity, extent, kinetics, dynamics, or type of a biologic's or cell's optical or bioimpedance response upon stimulation with an exogenous stimuli, such as a ligand candidate compound, a viral particle, a pathogen, a surface or culture condition, or like entity. Such terms can also include non-biologic or non-cell responses to stimuli or reactions to stimuli.

"Attach," "attachment," "adhere," "adhered," "adherent," "immobilized," or like terms generally refer to immobilizing or fixing, for example, a surface modifier substance, a compatibilizer, a cell, a ligand candidate compound, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with a cell anchoring material, or like entity.

"Adherent cells" refers to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell, a cell line, or a cell system, such as a prokaryotic or eukaryotic cell, which weakly interacts, associates with, or contacts the surface of a substrate during cell culture. However, these types of cells, for example, human embryonic kidney (HEK) cells, tend to dissociate easily from the surface of a substrate by physically disturbing approaches, such as washing or medium exchange. "Suspension cells" refer to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" can also refer to the culturing of cells derived from multicellular eukaryotes, especially animal cells, including the culturing of complex tissues and organs.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of more than one type of cells (or differentiated forms of a single type of cell), which interact with each other, thus performing a biological or physiological or pathophysiological function. Such cell system includes, for example, an organ, a tissue, a stem cell, a differentiated hepatocyte cell, or like systems.

"Stimulus," "therapeutic candidate compound," "therapeutic candidate," "prophylactic candidate," "prophylactic agent," "ligand candidate," "ligand," or like terms refer to a molecule or material, naturally occurring or synthetic, which is of interest for its potential to interact with a cell attached to the biosensor or a pathogen. A therapeutic or prophylactic candidate can include, for example, a chemical compound, a biological molecule, a peptide, a protein, a biological sample, a drug candidate small molecule having, for example, a molecular weight of less than about 1,000 Daltons, a drug candidate biologic molecule, a drug candidate small molecule-biologic conjugate, and like materials or molecular entity, or combinations thereof, which can specifically bind to or interact with at least one of a cellular target or a pathogen target such as a protein, DNA, RNA, an ion, a lipid, or like structure or component of a live-cell.

"Biosensor" or like terms generally refer to a device for the detection of an analyte that combines a biological component with a physicochemical detector component. The biosensor typically consists of three parts: a biological component or element (such as a cellular target, tissue, microorganism, pathogen, live-cell, or a combination thereof), a detector element (operating in a physicochemical manner such as optical, piezoelectric, electrochemical, thermometric, or magnetic), and a transducer associated with both components. In embodiments, an optical biosensor can comprise an optical transducer for converting a molecular recognition or molecular stimulation event in a cellular target, a live-cell, a pathogen, or a combination thereof into a quantifiable signal.

"Include," "includes," or like terms refers to including but not limited to, that is, inclusive and not exclusive.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, concentrates, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto are intended to include equivalents of these quantities with or without the "about" modifier.

"Optional," "optionally," or like terms refer to the subsequently described event or circumstance can or cannot occur, and that the description includes instances where the event or circumstance occurs and instances where it does not. For example, the phrase "optional component" means that the component can or can not be present and that the disclosure includes both embodiments including and excluding the component.

"Consisting essentially of" in embodiments refers, for example, to a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agent, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, excessively thick layers of the chelating polymer as a surface layer, such as greater than about 1,000 nm, because of the penetration depth limits of the evanescent wave, and like considerations.

The indefinite article "a" or "an" and its corresponding definite article "the" as used herein means at least one, or one or more, unless specified otherwise.

Abbreviations, which are well known to one of ordinary skill in the art, may be used, for example, "h" or "hr" for hour or hours, "g" or "gm" for gram(s), "mL" for milliliters, "rt" or "RT" for room temperature, "nm" for nanometers, and like abbreviations.

"Weight percent," "wt %," "percent by weight," or like terms with reference to, for example, a component, unless specifically stated to the contrary, refer to the ratio of the weight of the component to the total weight of the composition in which the component is included, expressed as a percentage.

Specific and preferred values disclosed for components, ingredients, additives, cell types, antibodies, His-tagged entities, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

Polymer gels that have been previously described which can immobilize biomolecules on LID biosensors that are made of, for example, a polysaccharide, such as dextran, or a synthetic polymer, such as polyacrylic acid, see, for example, U.S. Pat. No. 5,436,161 (assigned to BIAcore), and EP 0,226,470 patent (the "'470 patent") entitled "Materials and methods for microchemical testing," J. A. Bosley, et al., (assigned to Unilever).

Among the numerous types of polymer gels, one frequently used is based on carboxymethyl dextran as described, for example, in S. Lofas, et al., "A Novel Hydrogel Matrix on Gold Surfaces in Surface Plasmon Resonance Sensors for Fast and Efficient Covalent Immobilization of Ligands," *J. Chem. Soc., Chem. Commun.*, 1990, 21, 1526-1528, and the aforementioned U.S. Pat. No. 5,436,161. This carboxymethyl dextran based gel has limited capture capacity due to its molecular weight ($M_w$ 500,000 g/mol for the CM5 sensor chip available from BIAcore) which makes the height or thickness of the final gel unsuitable for very high protein capture capacity.

A related approach was described in PCT Publication No. WO 2007/049269 (Applicant Bio-Rad). This publication mentions binding layers comprising a polysaccharide substituted with carboxylic acid groups exhibiting high performance in the binding of ligand molecules and in the interaction with analyte molecules. The polysaccharide is modified by reaction with an alanine spacer. This publication mentions that the spacer modification allows more efficient activation of the carboxylic acid groups of the spacer compared to activation of the carboxylic acid groups of a known carboxymethylated polysaccharide. This publication also mentions that synthetic polymers, like poly(acrylic acid) or poly(methacrylic acid), exhibit much more efficient activation and subsequent immobilization. However, the ligand molecules exhibited low activity perhaps due to lower "biocompatibility" of these polymers (see p. 13, lines 5-9).

The problem of low immobilization capacity of an NTA monolayer has been studied by Gershon (P. D. Gershon, et al., "Stable Chelating Linkage for Reversible Immobilization of Oligohistidine Tagged Proteins in the Biacore Surface Plasmon Resonance Detector," *Journal of Immunological Methods*, 1995, Vol. 183, pgs. 65-76), who proposed an SPR chip coated with NTA modified dextran hydrogel. This chemistry is now commercially available from BIAcore under the trade name NTA-chip. The dextran matrix provides a 3D hydrogel (typically 100 nm thick) which allows capturing significantly much more protein than observed with surface chemistry based on an NTA monolayer (SAM). Although this NTA sensor chip is particularly useful for large molecule interaction studies, it remains unsuitable for small molecule interactions due to the limited amount of immobilized proteins and to high protein dissociation.

To overcome the drawback of protein leaching, another strategy has described how to combine affinity capture and covalent coupling to ensure good protein stability and prevent protein dissociation, see WO 2004/046724; U.S. Patent Publication No. US2006/0014232, to Inagawa, et al., "Immobilization Method"; and F. S. Willard, et al., "Covalent Immobilization of Histidine-Tagged Proteins for Surface Plasmon Resonance," *Anal. Biochem.*, 2006, Vol. 353, pgs. 147-149. However, this method suffers from an important drawback: as covalent coupling and affinity capture are realized at the same time, protein attachments are performed in an uncontrolled manner by reaction between reactive groups of the surface and reactive groups from the proteins without any specificity. This is particularly unsuitable because the main reason to select capture of protein by affinity is that the protein is attached to the sensor surface by means of only the tag having a well defined position and not by a non-specific chemical reaction. Another strategy was applied using the NTA-chip. After immobilization of proteins on the NTA-chip, an EDC/NHS treatment was performed on immobilized biomolecules to create covalent bonds between the substrate and the biomolecules (see M. A. Wear, et al., "A Surface Plasmon Resonance-Based Assay for Small Molecule Inhibitors of Human Cyclophilin A," *Anal. Biochem.*, 2005, Vol. 345, pgs. 214-226). Unfortunately, even if no dissociation of biomolecules from the substrate was observed after the EDC/NHS treatment, protein leaching appears to be important during the activation step. Coupled with the inherently poor immobilization capacity of the chemistry of known methods, protein leaching or loss from the surface further contributes to a decrease in the amount of immobilized protein on the substrate. Finally, the low capacity of biomolecules captured appears to be a primary drawback that prevents this chemistry from being suitable for small molecule recognition events.

The LID method is based on the local change of refractive index induced by the adsorption of a ligand onto an immobilized target such as a receptor(s).

The issue of low target immobilization on a biosensor and low specific ligand binding activity on a biosensor can be overcome by the selectively chemically and biologically functionalized surfaces of the disclosure having high biochemical target immobilization on a biosensor and high specific ligand binding activity with the surface bound biochemical target.

The surface disposition of the biosensor article of the disclosure enhances the resulting signal by increasing the immobilized target or immobilized receptor density, i.e., the number of the receptors immobilized on the biosensor which in turn provides increased capture capacity for targeted ligands, and by providing increased activity or availability of the immobilized receptor.

In embodiments, the surface chemistry of the disclosure may be compatible with Dual Polarized Intereferometry (DPI), which is another type of LID sensor, or surface plasmon resonance (SPR) type sensors.

In embodiments, the disclosure relates to a method for efficiently immobilizing biomolecules, such as proteins, for example, on a substrate or sensor surface. The disclosure is particularly useful in the field of biosensors for label independent detection (LID). The disclosure relates more particularly to surface chemistry of LID biosensors and to methods of preparation and use.

In the analysis of the biomolecular recognition events with LID, at least one biomolecule must be immobilized on the substrate as close as possible to the wave guide surface and a second molecule partner or complement, which recognizes or is recognized by the immobilized biomolecule, and reacts or binds to the immobilized molecule. Binding locally modifies the refractive index due to the local mass increase and is detected as a wavelength shift or SPR signal.

For LID techniques based on such a local change of refractive index induced by the adsorption of the ligand onto the immobilized receptors, proper surface chemistry can enhance the signal by increasing the number of the receptors immobilized so as to capture a greater amount of ligands. Moreover, the surface chemistry must retain the receptor firmly attached on the sensor surface. Indeed, desorption of the receptor leads to an unacceptable huge variation of the wavelength shift or the SPR signal which may totally hide the binding of the small molecule, such as a new drug entity. To prevent such receptor desorption, covalent attachment of the receptor on the sensor is commonly used. But in some cases, covalent immobilization can lead to partial or complete loss of protein activity, due to random orientation, structural deformation, and like considerations.

To achieve a high binding response, it is desirable to have a high level of immobilized biomolecules, and equally desirable to have immobilized biomolecules available for the binding event. This means that biomolecules must be in a native or active conformation, and well-oriented on the sensor surface to prevent, for example, steric hindrance effects which generally lead to a reduced binding response.

To obtain such biomolecule availability and good orientation, immobilization through affinity capture is generally preferred to covalent attachment. Such affinity capture methods are, for example, based on biotinylated molecules captured by streptavidin or avidin previously attached on the surface, or histidine-tagged molecules captured by a metal ion previously immobilized on the surface. Both of these methods require the addition of a tag to the biomolecule for the immobilization step but can provide excellent availability and good orientation of the immobilized biomolecules. However, for immobilized histidine tagged (His-tag) molecules, desorption is usually observed and can hide binding of small molecules.

To overcome the inherent drawbacks of the two approaches, the present invention provides a sequential method for providing biosensor surfaces capable of immobilizing bioentities and like substances (e.g., receptors, proteins) by affinity capture at high density and high stability, followed by a chemical treatment leading to covalent attachment of the receptors on the substrate.

In embodiments, the disclosure provides a biosensor article comprising:
a substrate having polymer on the substrate surface, the polymer comprises:
a polymer of formula (I)

$$\left(\begin{array}{c}W\\|\\R''\\|\\X\\|\\O=C\\|\\R'-C-\\|\\R\end{array}\right)_x \left(\begin{array}{c}R\diagdown X\diagup R\\|\\O=C\\|\\R'-C-\\|\\R\end{array}\right)_y \left(\begin{array}{c}\\R\\|\\R'-C-\\|\\O=C\\|\\S\end{array}\right)_z \quad (I)$$

having at least one of: a metal-ion chelating group (x), an ionizable group (y), and a surface substantive group (z), where R is hydrogen or a substituted or unsubstituted, linear or branched, monovalent hydrocarbyl moiety having from 1 to 6 carbon atoms;

R' is a substituted or unsubstituted, linear or branched, divalent hydrocarbyl moiety resulting from copolymerization of an unsaturated monomer, for example, acrylic acid, acrylamide, or a combination thereof, having from 1 to 18 carbon atoms;

R" is a substituted or unsubstituted, linear or branched, divalent hydrocarbyl moiety having from 1 to 20 carbon atoms;

S comprises at least one point of association or attachment to the substrate;

W comprises at least one metal-ion chelator moiety, for example, a bi-dentate group, a tri-dentate group, a tetra-dentate group, and like groups, or a combination thereof;

X is an —NH—, —NR—, or O; and the mole ratio of x:(y+z) groups is from about 2:8 to about 8:2.

In embodiments, S can be, for example, a portion of a substrate surface group or modified surface group that can covalently bond to the polymer, or can be, for example, a functional group of the polymer that bonds to or otherwise associates with the substrate surface. S can be, for example, at least one of: a metal oxide, a mixed metal oxide, a polymer, a composite, or a combination thereof; a surface modified substrate; or a combination thereof, for example, $Nb_2O_5$, $SiO_2$, $Nb_2O_5/SiO_2$, cyclic olefin copolymer, and like points of attachment to a substrate. S can be, for example, an aminosiloxane treated glass or plastic substrate. The S can additionally or alternatively be, for example, a surface coating modified substrate, such as with known silanes GAPS, APS, MOPS, and like modifiers, or a combination thereof.

In embodiments, W can be, for example, at least one metal-ion chelate group, and is an incipient binding site for a biomolecule having at least one tag, that is W can be, for example, at least one bi-dentate group, tri-dentate group, or tetra-dentate group, such as a metal-ion chelating group in the absence of a metal-ion, and can be, for example, an active binding site for a biomolecule having at least one tag in the presence of a chelated metal ion. The W chelating group can be, for example, at least one iminodiacetic acid (IDA), nitrilotriacetic acid (NTA), triazacyclononane (TACN), amino ethylethano lamine, triethylenetetramine, 2-hydroxypropane-1,2,3-tricarb oxylate (citrate), and like bis-, tris-, and multi-dentate chelating substituents, derivatives thereof, or a combination thereof. The metal-chelate group can be mono-NTA, bis-NTA or tris-NTA, tetrakis-NTA, poly-NTA, and like groups, or a combination thereof. The ionizable groups can be, for example, carboxylic acid groups, and like groups, or a combination thereof.

In embodiments, the X can be, for example, —NH— (an amic-acid), —O— (a carboxylic acid, carboxy ester, hemi-ester), and like groups, or a combination thereof. In embodiments, a particularly useful X is —NH—.

In embodiments, the mole ratio x:(y+z) can be, for example, from about 2:8 to about 8:2; from about 2:1 to about 1:2; and from about 1 to about 1, including all intermediate values and ranges. The mole ratio of x:(y+z) can preferably be, for example, about 1:1, such as found in the exemplary PAA:NTA material disclosed herein.

In embodiments, the article can further include the polymer having at least one metal-ion complexed with W, the at least one metal-ion comprising at least one metal-ion selected from, for example, Ni, Cu, Zn, Co, Fe, or a combination thereof. The article can further include the polymer having a His-tagged entity associated with the complexed metal-ion comprising at least one of a natural or synthetic oligonucleotide, a natural or synthetic nucleic acid (e.g., DNA or RNA), a natural peptide, a natural or synthetic peptide optionally comprising one or more modified or blocked amino acids, an antibody, a hapten, a biological ligand, a protein membrane, a lipid membrane, a protein, a small molecule having a molecular weight of less than about 500 Daltons, a cell, or a combination thereof, or a conjugate thereof. The article can further include the polymer having a ligand conjugated with the associated His-tagged entity. The ligand can be, for example, at least one of a stimulus, a therapeutic candidate, a prophylactic candidate, a prophylactic agent, a chemical compound, a biological molecule, a peptide, a protein, a biological sample, a small molecule having a molecular weight of less than about 500 Daltons, a biologic drug molecule candidate, a drug candidate small molecule-biologic conjugate, a pathogen, a cell, or combinations thereof.

In embodiments, the polymer of formula (I) can have a specific structure incorporating, for example, R is hydrogen, or a substituted or unsubstituted alkyl having from 1 to 4 carbon atoms;

R' is a divalent hydrocarbyl moiety having from 1 to 10 carbon atoms;

R" is a substituted or unsubstituted, divalent hydrocarbyl moiety having from 2 to 6 carbon atoms;

S is an unsaturated silane or mercapto silane substrate;

W can be, for example, at least one iminodiacetic acid, nitrilotriacetic acid, triazacyclononane, aminoethylethanolamine, triethylenetetramine, 2-hydroxypropane-1,2,3-tricarboxylate, and like substituents or derivatives or salts thereof, or a combination thereof;

X is —NH—; and the mole ratio x:(y+z) is from about 2:1 to about 1:2.

In embodiments, the article can include the polymer of formula (I) having, for example, the mole ratio x:(y+z) of about 1:1. The polymer on the substrate surface can be, for example, a continuous or discontinuous layer or film having a thickness of from about 20 to about 1,000 nm.

In embodiments, the disclosure provides a method for making a biosensor article having a polymer of formula (I), and as illustrated in FIG. 1, comprising:

Path A comprising:

contacting a substrate surface having an associated or attached polymer of formula (II):

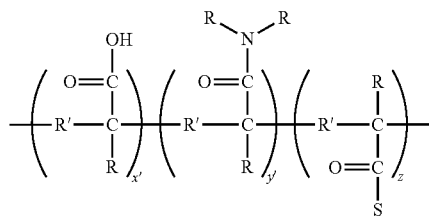
(II)

and an activating agent to form an activated polymer (not shown) having carboxy groups modified with activating substituents; and contacting the resulting activated polymer with a chelate group former to form a polymer of formula (I), such as a specific polymer of formula (IV):

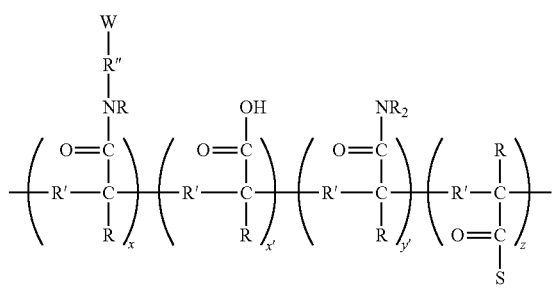
(IV)

where x' and y' represent residual ionizable groups which remained after contact with the activating agent and the chelate group former.

A more specific polymer of formula (IV) is the surface bound or associated polymer of formula (V):

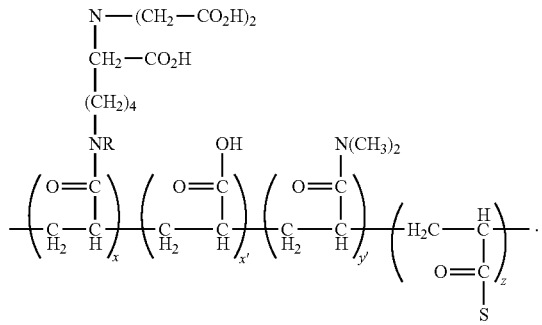
(V)

In embodiments, in Path A, the activating agent can be, for example, selected from 1-ethyl-3-(3-dimethyl aminopropyl carbodiimide hydrochloride) (EDC), dicyclo hexyl carbodiimide (DCC), N,N' carbonyl diimidazole (CDI), 1-cyclohexyl-3-(2-morpholino ethyl)carbodiimide (CMC), diisopropylcarbodiimide (DIC), Woodward's reagent K, and like activating agents, or a combination thereof. Preferred activating agent is EDC/NHS and EDC/sulfoNHS, preferably at a concentration from 200/50 mM to 20/5 mM. NHS is N-hydroxysuccinimide (NHS) and Sulfo-NHS is N-hydroxysulfosuccinimide.

The attached polymer formula (II) can be comprised of a mixture of a first acrylamide monomer and a second acrylamide monomer having the metal-ion chelator moiety. The associated or attached polymer of formula (II) can be obtained by contacting the substrate with a preformed polymer, for example, of formula (III):

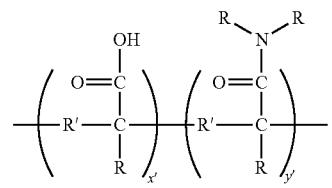
(III)

comprised of a mixture of an acrylic acid monomer (x') and an acrylamide monomer (y'), or like monomers.

Figure 2:
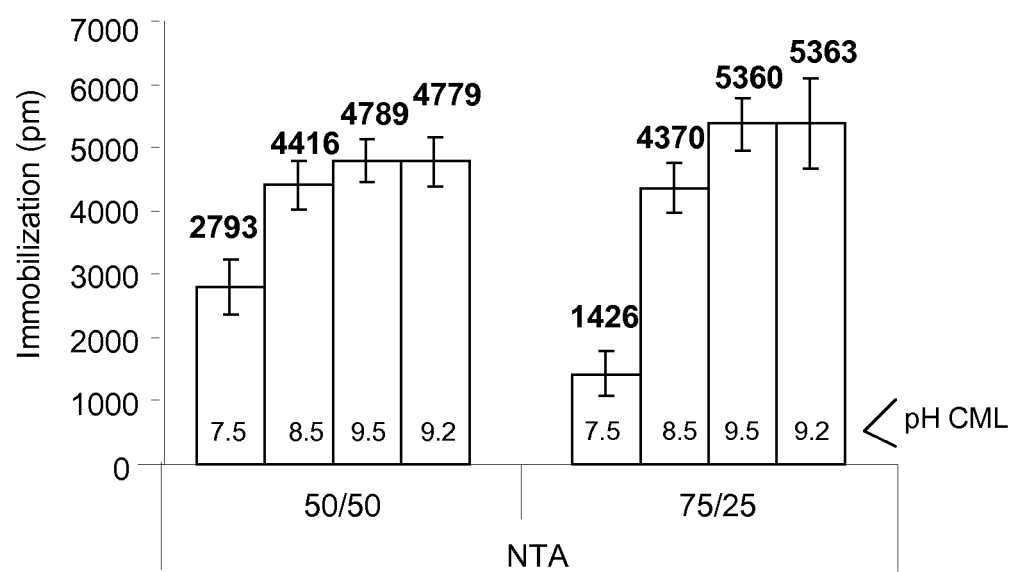
FIG. 2 shows results for his-tag CAII immobilization measured with an Epic® biosensor on PAA-NTA modified surfaces prepared with different CML solution concentrations and at different pH values.

In embodiments, the disclosure provides an alternative in-situ method for making a biosensor article having a polymer of formula (I), comprising:

Path B comprising:

polymerizing a mixture of at least one acrylamide monomer having at least one metal-ion chelator moiety, and an unsaturated organosilane modified surface to form a attached or associated polymer of formula (I) and as illustrated in FIG. 2.

In Path B, the polymerizing can be accomplished, for example, with actinic radiation, heating, a free radical initiator, or combination thereof.

A notable difference between the associated or attached polymer formulas resulting from preparative processes of Path A and Path B is that in Path B there is typically little or no residual ionizable carboxylic acid groups (x') in the surface polymer as shown in the accompanying polymer of formula (VI):

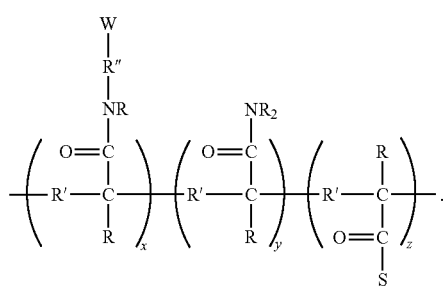
(VI)

This structure difference can be used to design or select particularly useful or effective polymer compositions and properties for specific immobilization targets.

In embodiments, in Path B the at least one acrylamide monomer can be, for example, a mixture of acrylamide monomers comprising a first acrylamide and a second acrylamide having the metal-ion chelator moiety. The first acrylamide monomer can be, for example, an acrylamide or alkyl substituted acrylamide, such as: Acrylamide, methacrylamide, 3-Acryloylamino-1-propanol, N-(Hydroxymethyl)acrylamide, a dialkyl acrylamide, such as N,N-Dimethylacrylamide, N,N-dimethyl(meth)acrylamide, N-Isopropylmethacrylamide, N-[Tris(hydroxymethyl)methyl]acrylamide, N-Acryloylamido-ethoxyethanol, N-Hydroxyethyl acrylamide, N-Isopropylacrylamide, or a combination thereof. The second acrylamide monomer having the metal-ion chelator moiety can be, for example, a chelate substituted acrylamide, a chelate substituted alkyl acrylamide, such as a nitrilotriacetate (NTA) substituted acrylamide, NTA substituted (meth)acrylamide, and like chelate containing acrylamides, or a combination thereof.

In Path B the metal-ion chelator moiety can be, for example, iminodiacetic acid (IDA), nitrilotriacetic acid (NTA), nitrilotriacetate, triazacyclononane, aminoethylethanolamine, triethylenetetramine, 2-hydroxypropane-1,2,3-tricarboxylate, and like substituents or derivatives thereof, or a combination thereof; and the organo silane modified surface can be, for example, methacryloxypropyltrimethoxysilane (MOPS), Vinyltrimethoxysilane, Vinyltriethoxylsilane, Allyltrimethoxysilane, Allyltriethoxysilane, Trimethoxy(7-octen-1-yl) silane, Octenyltrichlorosilane, 3-(Trichlorosilyl)propyl methacrylate, Allyltrichlorosilane, Trichlorovinylsilane, 3-(Diethoxymethylsilyl)propyl methacrylate, 3-(Trimethoxysilyl)propyl acrylate, Diethoxy(methyl)vinylsilane, Dimethoxy(methyl)vinylsilane, Ethoxydiphenylvinylsilane, and like unsaturated organosilane acrylates or acrylamides, a thiol substituted alkoxy silane, such as 3-Mercaptopropyl)triethoxysilane, 3-Mercaptopropyltrimethoxysilane, or any combination thereof.

In embodiments, in either Path A or Path B, the processes can further include contacting the polymer of formula (I) with a His-tagged entity to form a His-tagged entity modified polymer substrate or biosensor. The resulting His-tagged entity modified polymer substrate can be further modified by, for example, contacting the His-tagged entity modified substrate with a covalent bonding agent, for example, to further secure the entity to the coated substrate, and then optionally treating with a blocking agent, for example, ethanolamine or like agents, to block residual or remaining activated esters. The method can further include contacting the bonding agent treated His-tagged entity modified substrate with a ligand to form a substrate having a His-tagged entity modified biosensor having at least one bound ligand.

In Path A or Path B, the first acrylic monomer can be present in the polymer, for example, in from about 20 to about 80 mol % and the second acrylic monomer having the metal chelate moiety can be present in the polymer of formula (I), for example, in from about 80 to about 20 mol % or wt % based on the total mol % or wt % of monomers in the copolymer.

In embodiments, in Path B, the first acrylamide monomer can be present in the polymer in from about 20 to about 80 mol % and the second acrylamide monomer having the metal chelate moiety is present in from about 80 to about 20 mol % based on the total mol % of monomers in the copolymer.

In embodiments, the first acrylamide monomer can be present in the polymer, for example, in from about 25 to about 75 mol %, from about 30 to about 70 mol %, and from about 35 to about 65 mol %, based on the total mol % of monomers in the copolymer, including intermediate values and ranges. The second acrylamide monomer having the metal chelate moiety can be present, for example, in from about 75 to about 25 mol %, from about 70 to about 25 mol %, from about 65 to about 30 mol %, from about 55 to about 30 mol %, and from about 50 to about 35 mol % based on the total mol % of monomers in the copolymer, including intermediate values and ranges. 40 to 60 mol % of the first acrylamide and 60 to 40 mol % of the second acrylamide is one preferred embodiment.

In embodiments, the disclosure provides a method for performing an assay of a ligand, the method comprising:
contacting a ligand and the aforementioned His-tagged entity modified substrate such that if the ligand binds to the His-tagged entity, then:
detecting the ligand-induced response of the biosensor.

In embodiments, the disclosure provides an article by the disclosed preparative methods that can be used, for example, in a biosensor or a cell culture.

In embodiments, the present disclosure can be accomplished by, for example, performing the polymerization directly on the substrate surface, also known as "in-situ" polymerization. This approach was used for the preparation of a polymer hydrogel for biological assay applications. One strategy to achieve an "in situ" polymer hydrogel was based on polymer brushes made from the surface ("grafting-from" strategy) where the polymeric chains are attached to a single or only a few points on the surface. For example, poly(acrylic acid) (PAA) polymer was prepared using controlled radical polymerization or Atom Transfer Radical Polymerization (ATRP) on gold or silica surfaces. A typical thickness of this polymer hydrogel layer after swelling in DI water was, for example, about 100 nm. The polymer was then modified with nitrilotriacetate (NTA) by activation with EDC/NHS (see for example, Jain, P, et al., "High capacity purification of his-tagged proteins by affinity membranes containing functionalized polymer brushes", *Biomacromolecules*, 2007, 8, 3102-3107; and Yu T, et al., "Functional hydrogel surfaces: binding kinesin based molecular motor proteins to selected patterned sites," *Advanced functional materials*, 2005, 15, 1303-1309). A similar approach was described using nitriloacetate to modify poly(HEMA) hydrogel (see Dai J, et al., "High capacity binding of proteins by poly(acrylic acid) brushes and their derivatives", *Langmuir*, 2006, 22, 4274-4281).

These PAA polymer hydrogels exhibit an improved immobilization capacity compared to self-assembled monolayer (SAM) but they were not intended for screening application, especially for small molecule recognition. These approaches did not provide a clear solution to the protein leaching shortcoming of NTA affinity chemistry. Moreover, the preparative process is complicated by relying upon a specific polymerization initiator anchored to the substrate, and a complex polymerization technique (i.e., controlled radical polymerization like ATRP or RAFT).

To overcome this limitation, an alternative to "in situ" polymerization was based on the direct reaction between monomers in solution and double bond reactive groups previously attached to the substrate. This method provides advantages compared to dip coating methods for the grafting of reactive polymer, for example, reduced polymerization time, fewer reagents used, and easier scale up. For example, a polymerization of HEMA and NTA methacrylate monomer was performed easily and quickly (e.g., a few seconds total reaction time) using UV activation to provide an NTA polymer hydrogel having a promising immobilization capacity (see Cullen S P, et al., "Polymeric brushes as functional templates for immobilizing ribonuclease A: study of binding kinetics and activity", *Langmuir*, 2008, 24, 913-920). Although the authors mentioned potential biosensor and biochip applications they provided no details regarding actual implementation of these applications. The reference was silent regarding protein leaching.

In embodiments, the present disclosure provides an affinity surface based on a polymer hydrogel prepared by improved processing, such as rapid, easy-to-prepare, low reagent consumption, which provides a very high immobilization capacity surface that is compatible with label free detection methods. The surface provides excellent stability for complexed NTA-Ni-histidine and the covalent attachment reaction prevents any protein dissociation.

In embodiments the disclosure provides a process for preparing a sensor for label-free detection having a metal/chelate surface.

In embodiments the metal/chelate surface can be prepared by a process comprising:

forming a (meth)acrylic gel having metal chelating groups in-situ in the presence of a copolymerizable tie layer; and In embodiments the disclosure provides an assay method comprising:

immobilizing a biomolecule on the resulting metal/chelate surface comprising contacting the surface with a biomolecule and thereafter treating the immobilized biomolecule on the surface to afford at least one additional covalent interaction between the immobilized biomolecules and the sensor surface.

In embodiments, the present disclosure addresses the needs described above by providing a sensor for label free detection having a metal-ion chelate surface chemistry comprising an in-situ formation of a (meth)acrylic gel having metal chelating groups; using a copolymerizable tie layer. The disclosure also provides an assay method performed in a second step after biomolecular immobilization, based on a treatment permitting covalent interactions between the immobilized biomolecules and the biosensor surface.

Useful tie layers can be, for example, an alkoxysilane, a chlorosilane, or a combination thereof, which can copolymerize or react with the (meth)acrylic monomers. Such silanes include, for example, those bearing a vinyl group, a (meth)acrylic acid ester group, a (meth)acrylamide group, and like groups. An especially useful silane is, for example, methacyloyloxypropyl trimethoxysilane.

In embodiments, the mixture to be polymerized in-situ can contain, for example, (meth)acrylic acid and acrylamide, or like monomers (FIG. 1A), or NTA modified (meth)acrylamide monomer and acrylamide (FIG. 1B), or like monomer mixture combinations.

When the monomer mixture to be polymerized in-situ contains (meth)acrylic acid and acrylamide derivatives, the chelating ligand group selected can be, for example, a macrocyclic ligand, such triaza-cyclononane, or a non-cyclic chelating ligand group, such as iminodiacetic or nitrilotriacetic. A particularly useful chelating ligand group is nitrilotriacetic group because of, for example, its availability, its ease of preparation, its high metal ion binding constant, and like considerations. The metal/chelate group can be, for example, mono-NTA, bis-NTA, tris-NTA, tetrakis-NTA, or poly-NTA. The NTA/modified in-situ formed (meth)acrylic gel can be obtained by reaction between carboxylic groups of the copolymer gel and one reactant bearing at least one NTA group, and at least one thiol, hydroxyl, or amino group that is able to react with the activated carboxylic groups leading to the formation of, thioester, ester, imide or amide groups respectively. The reactant bearing at least one NTA group can be selected from, for example, compounds described by Hochuli (see Hochuli, et al., U.S. Pat. No. 4,887,830; "Metal Chelate Resins," European Patent No. EP 0 253 303B1, "Neue Metallchelatharze," and J. Chromatogr., 1987, Vol. 411, pgs. 177-184), and more preferably the compound is N,N bis-(Carboxymethyl)-L-Lysine or a salt form, such as the N,N bis-(Carboxymethyl)-L-Lysine disodium salt mono hydrate.

In the present disclosure it was unexpectedly noted that the pH used for grafting the chelating group to the polymer matrix can significantly influence the resulting capacity of the surface for immobilization. For example, a high pH of from about pH 7 to 10 leads to high protein immobilization. A specific high pH for high protein immobilization is, for example, pH=9.2. The thickness of the NTA/copolymer gel on the sensor surface can be, for example, from about 5 to about 200 nm.

When the monomer mixture to be polymerized in-situ contains NTA modified (meth)acrylamide and acrylamide, or like monomer derivatives, a similar NTA based polymer hydrogel can be obtained in a single step since a conjugation step between carboxylic groups of the polymer matrix and the CML compound is unnecessary.

Surprisingly, it was noted that such chemistry, based on an in-situ formed (meth)acrylic gel bearing NTA groups followed by a second step which creates covalent bonds between the immobilized biomolecules and the in-situ generated (meth)acrylic gel, overcomes the aforementioned problems by providing a very high protein immobilization capacity and free of protein dissociation or protein leaching which makes this surface chemistry highly compatible with low molecular weight drug screening using label-independent detection (LID).

It was also surprisingly noted that the ratio between these monomers (dimethylacrylamide and acrylic acid) can be significant to obtain high protein immobilization activity. Indeed, the number or percentage of acrylic acid monomers in the polymer matrix was reproducible and compatible with the Epic® sensor methodologies and correlated with known Epic® responses. So, it is significant to select the best polymer matrix to maintain the biological activity of the protein when in contact with the surface, and to realize large amounts of protein capture. Conservation of a high biological activity assures that a large number of ligands can interact with the immobilized protein thus increasing the assay sensitivity.

In embodiments, the disclosure provides methods for preparing sensors having an NTA-based polymer hydrogel.

In embodiments, the disclosure provides methods for preparing sensors having high protein immobilization capacity and which can provide a high ligand binding response, where high immobilization capacity and high ligand binding response refers to comparable or greater than known sensors having known protein immobilization capacity and ligand binding response. The disclosed sensors can provide, for example, a 4000 picometer (pm) immobilization response and a 20 pm binding response. On Epic®, 1 pm response corresponds to about 5 pg/mm$^2$ of adsorbed molecules (5 pg/mm$^2$/pm). So 4000 pm immobilization response is equivalent to 20 ng/mm$^2$ immobilized proteins and 20 pm biding response is equivalent to 100 pg/mm$^2$ immobilized proteins.

In embodiments, the disclosed surfaces can overcome the issue of protein dissociation or protein surface leaching that has been observed with prior art surface chemistries by, for example, including a covalent bonding step to fix the protein to the modified surface.

In embodiments, the disclosed surface chemistry is straight forward to implement and is compatible with virtually any label-free detection platform, such as based on SPR, resonant gratings, Epic® sensor plates, dual polarization interferometry, with or without a micro-fluidic aspect.

In embodiments, the disclosed surfaces can have excellent shelf-life, such as from about one month to about twelve months or more. In embodiments, the disclosure provides surfaces and method which permit immobilization of proteins over a wide pH range, and especially at a pH above the pI of proteins.

In embodiments, the disclosed preparative process affords significant reductions in solvent consumed in sensor manufacturing compared to, for example, a conventional dip coating process, such as from about 10 to about 98 weight percent solvent reduction.

In embodiments, the disclosed process is significantly faster, such as from about 5 to about 85% faster than usual polymer synthesis and dip coating process.

In embodiments, the disclosed preparative process can be easily adjusted, for example, by changing the relative weight ratio of the monomers in the mixture, to identify particularly useful polymer matrices for a particular bioassay.

From a commercial perspective, the PAA-NTA affinity surfaces of the disclosure emphasize that a PAA/DMA polymer matrix can be a platform for capture of proteins by amine coupling (PAA/DMA) or of his-tag labeled proteins by affinity interactions (after chemical modification to obtain PAA-NTA).

In embodiments, the present disclosure provides affinity based surface chemistry that has, for example, a very high immobilization capacity, which is compatible with label free detection, which provides a high stability NTA-Ni-histidine complex, and which prevents substantially any protein dissociation using a post-immobilization covalent attachment reaction prior to ligand detection.

One illustrative preparative procedure for making a biosensor article includes, for example, coating a suitable substrate, such as an insert or glass slide with a tie-layer or conversion coating, such as can be obtained by treatment with aminopropyl silane (APS). Next, the tie-layer treated substrate can be, for example, dip-coated in a solution or dispersion of the polymer, such as an PPA-DMAm (50:50) solution at a concentration of 1 mg/mL in DMSO:IPA=50/50=v:v, over about 10 min. The rinsed and dried polymer coated substrate is then treated with EDC/sNHS or like agent and then CML or like modifying compound, either neat or in a suitable solution such as a borate buffer, for about 30 min. The metal ion can be complexed with the polymer by, for example, the addition of a suitable metal salt solution, such as 40 mM $NiSO_4$ solution, and stirring for about 30 min.

In embodiments, the polymer can be, for example, a preformed derivatized product of an acrylic acid (AA) and an acrylamide (MAm) copolymer having a portion of the carboxy groups derivatized with a spacer (R"), at least one bi-dentate group such as a metal-ion chelator (W), and optionally a metal-ion ($M^{n+}$). In embodiments, the polymer can alternatively be prepared, for example, by contacting a copolymer modified surface and a compound having a spacer and a metal chelator (e.g., carboxymethyl lysine; CML also known as NTA), and then contacting the copolymer modified substrate having the attached spacer and a bi-dentate metal-ion chelator, and a metal-ion solution to form a copolymer modified substrate surface having at least some chelated metal ion.

Although not limited by theory, it is believed that surfaces modified with a copolymer of formula (I) can reversibly relax or unfold in certain solutions, such as buffer media, to provide an extended structure more akin to sea-weed attached to the bottom of lake by a single or very few points of attachment. The extended structure can provide a greater number of points where the metal ion may complex and thus where a tagged biomolecule or like entity can complex for immobilization.

In embodiments, the disclosure provides a method for using the disclosed biosensor article comprising:

contacting the substrate having the abovementioned metal-ion complexed polymer and a His-tagged entity target, such as a small molecule, Ab, protein, cell, and like entities, having at least one His-tag or label, for example, His-tagged carbonic anhydrase, to immobilize the His-tagged entity, and contacting the substrate having the immobilized His-tagged entity and a covalent bonding agent or stabilizing agent to form a substrate having a stabilized His-tagged entity.

The covalent bonding agent or stabilizing agent can be, for example, NHS/EDC, and like reagents or treatments. The stabilized intermediate product resulting from the contacting with the stabilizing agent need not be isolated. If desired, stabilized intermediate product can be used directly in covalent ligand capture and sensing. The method of use can further include contacting the substrate having the stabilized His-tagged entity, with a ligand to form a substrate having a His-tagged entity having a bound ligand, i.e., a ligand for the His-tagged entity or His-tag conjugate-former, e.g., small molecule, Ab, protein, cell, and like ligands.

In embodiments, contacting the substrate with a His-tagged entity, i.e., immobilization, can be accomplished at, for example, a pH of from about 3 to about 9. The contacting of the substrate with a His-tagged entity can be accomplished at, for example, a pH above the pI of the His-tagged entity.

In embodiments, the His-tagged entity immobilization can be, for example, greater than about 1,500 pm and the loss of immobilized His-tagged entity can be, for example, less than about 0.1 wt % of the total originally immobilized His-tagged entity, which increased immobilization and stability properties taken together provide a biosensor having a biosensor binding response greater than about 10 picometers (pm). The biosensor can be, for example, at least one of: a surface plasmon resonance biosensor, a waveguide resonant grating biosensor, an impedance biosensor, a mass spectrometry biosensor, and like devices, or a combination thereof.

When a LID biosensor such as grating resonant sensors or SPR-sensors are used, the evanescent field wave can only probe about the first 100 to about 200 nanometers from the surface making a micrometer thick gel unsuitable. Thus, biomolecules that have been captured in the gel beyond about 200 nm from the sensor surface are effectively invisible to the evanescent field wave, and any biomolecular recognition event occurring beyond about 200 nm is not detected. This situation yields unacceptably high biomolecule consumption, which further limits it's applicability for high throughput system (HTS) applications, such as those involving precious protein.

In embodiments, the disclosure provides a surface chemistry, based on synthetic polymers, which can be easily attached to a LID sensor surface, has very high immobilization capacity, provides good availability and activity of the immobilized biomolecule, and is compatible with label-free detection methodologies. The method of making is easy to implement, and is compatible with manufacture scale-up, e.g., does not require long polymerization times nor long washing times.

By using the described preparative method, a very reproducible layer on the surface of the substrate can be obtained which is fully compatible with commercially available LID systems such as the Epic® system (Corning Incorporated).

The polymer layer on the surface of the substrate provides enhanced capture of the biomolecules as demonstrated in the working examples. The nanoparticle layer on the surface of the substrate can be, for example, from about 10 to about 100 nm, as measured by, for example, SEM or AFM methods.

Because a very high immobilization level of protein can be obtained and a high activity of the protein established, the coated sensor article of the disclosure can be particularly suitable for detecting binding events occurring between proteins and very low molecular weight molecules, e.g., small molecules.

In embodiments, the sensor of the disclosure is compatible with high throughput screening (HTS) of drug or other small molecules due to the high binding response provided. Even very low molecular weight compounds, such as fragments having a molecular weight of less than about 500 Daltons, can be also screened using the sensor due to the high binding response.

In embodiments, the disclosure permits preparation of sensors for label-free detection using a low protein concentration which suggests that the cost per analysis can be substantially reduced compared to other LID techniques.

In embodiments, the disclosure provides a surface that is suitable for the attachment, growth, and assay of many types of cells, including strongly adherent cells such as Chinese hamster ovary (CHO) cells and human epithelial carcinoma A431 cells, intermediate adherent cells such as RMS13 cells, and weakly adherent cells such as human embryonic kidney (HEK) cells, or primary cells.

The disclosure provides methods to modify the surface of a biosensor so that the surface of these biosensors is compatible with and amenable to cell culture and subsequent cell assays. The disclosed method is suitable for oxidized metal thin film surfaces such as the ones used in resonant waveguide grating biosensors, or an un-patterned gold surface, such as those used in surface plasmon resonance (SPR), or a patterned gold surface, such as those used in electrical bioimpedance-based biosensors.

The disclosure may suitably comprise, consist of, or consist essentially of: a cell culture article as defined herein; a method for preparing the cell culture article as defined herein; and a method for performing an assay of a ligand as defined herein. In embodiments, the disclosure provides a cell culture article comprising: a substrate; an optional tie-layer attached to at least the substrate; and a bio-compatible layer of the disclosed polymer attached to the optional tie layer, to the substrate, or both.

Referring to the Figures, FIG. 1A shows a schematic representation of a surface modification of the disclosure to obtain a PAA/DMA matrix by performing: 1.) an EDC/sNHS activation, for example on a substrate modified with a PAA/DMAm copolymer having a 1:1 relative mole ratio (or 50:50 mol percent) of acrylic acid (AA) and dimethylamine acrylamide (DMAm); and 2.) carboxymethyl lysine (CML) addition to add the nitrilo tri-acetic acid complexing groups to form a surface bound (PMA-NTA) polymer. Thereafter, a third step may be accomplished (not shown) involving treatment of the PMA-NTA polymer with a nickel salt resulting in, for example, $Ni^{2+}$ ion complexation with the polymer modified surface.

BRIEF DESCRIPTION OF THE FIGURES

Figure 1B:
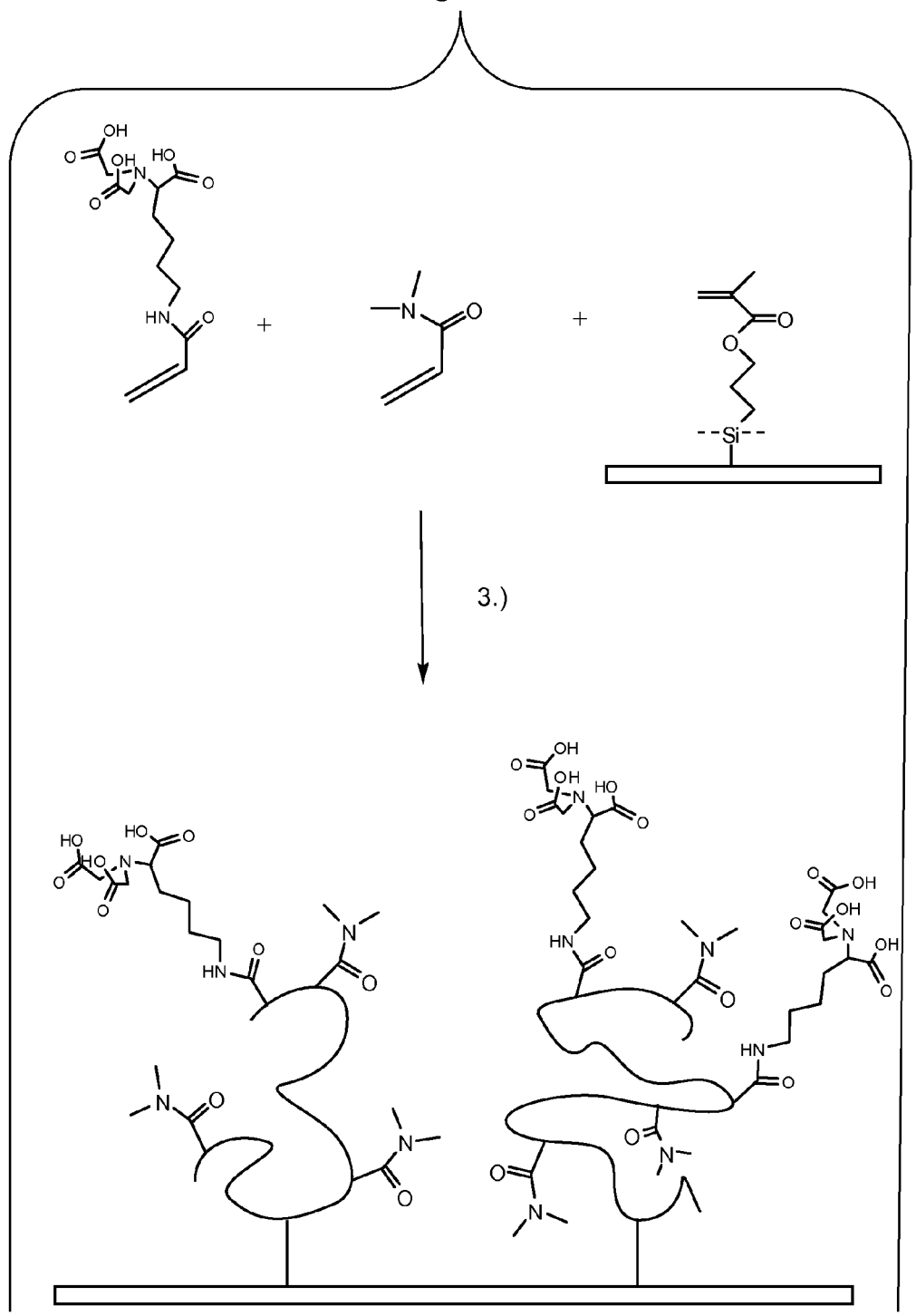
FIG. 1B shows a schematic of an alternative method for preparing the disclosed surface modification.

FIG. 1B shows an alternative route to obtain, in a single step, the PMA-NTA polymer modified surface of the disclosure, where a mixture of NTA-di(meth)acrylamide monomer and dimethylacrylamide (DMA) monomer is copolymerized with a reactive surface bound acrylate such as methacryloxypropyltrimethoxysilane (MOPS) and with, for example, 3.) ultraviolet radiation or like agents.

FIG. 2 is a graph showing his-tag CAII immobilization in hepes+salts pH=7.4 (50 micrograms/mL) on PAA-NTA polymer modified surfaces (50/50 or 75/25) (wt/wt) (AA/DMA as the starting monomers) that were prepared using CML solutions having different pH values on the PAA/DMA 50/50 matrix. The immobilization is influenced by the pH of the CML solution: the higher the pH (in the range 7<pH<9.5), the higher the observed immobilization level.

Figure 3:
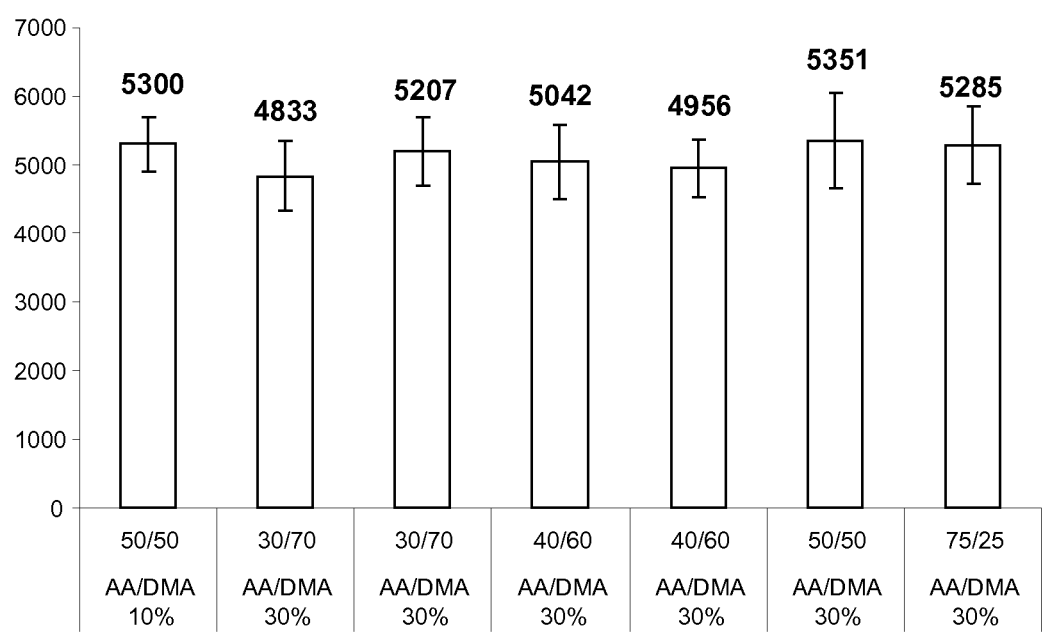
FIG. 3 shows his-tag CAII immobilization results measured with an Epic® biosensor on PAA-NTA modified surfaces having different ratios of AA/DMA.

FIG. 3 is a graph showing his-tag CAII immobilization in hepes+salts pH=7.4 (50 micrograms/mL) for different PAA-NTA chemistries based on different PAA/DMA matrixes (measured on an Epic® instrument). This graph shows the high immobilization capacity of PAA-NTA surfaces. The % given in this figure is by wt %.

Figure 4:
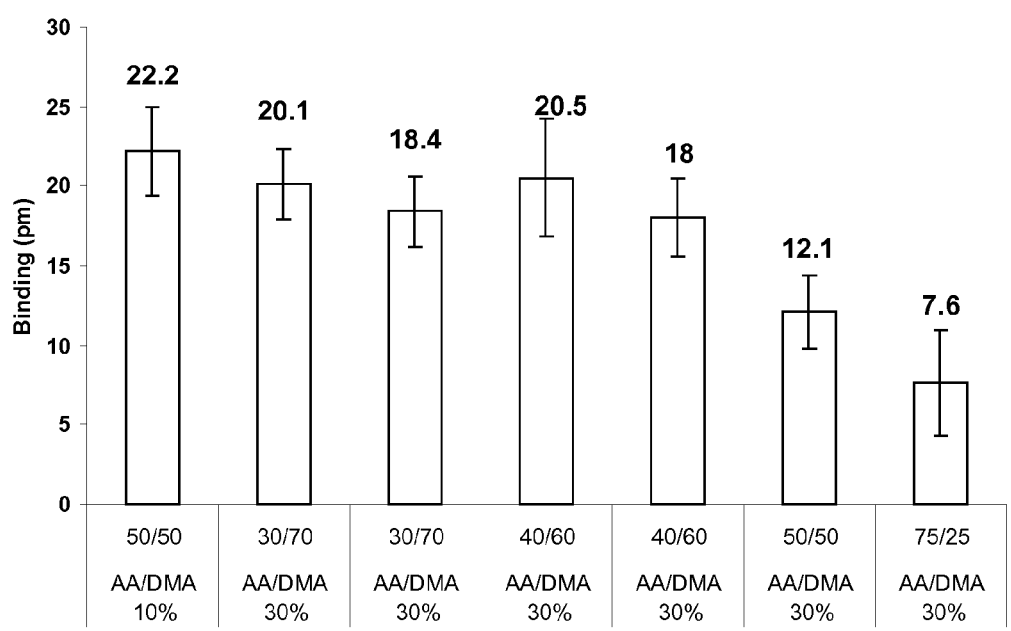
FIG. 4 shows furosemide binding on immobilized his-tag CAII modified surfaces measured with an Epic® biosensor on PAA-NTA modified surfaces having different ratios of AA/DMA.

FIG. 4 is a graph showing binding responses for furosemide ligand on immobilized his-tag CAII (measured on Epic® equipment). The graph demonstrates a significant influence of the monomer ratio in the polymer composition on binding response, that is as the AA content in the AA:DMA ratio increases or decreases from 1:1 (or 50/50) the ligand binding decreases.

Figure 5:
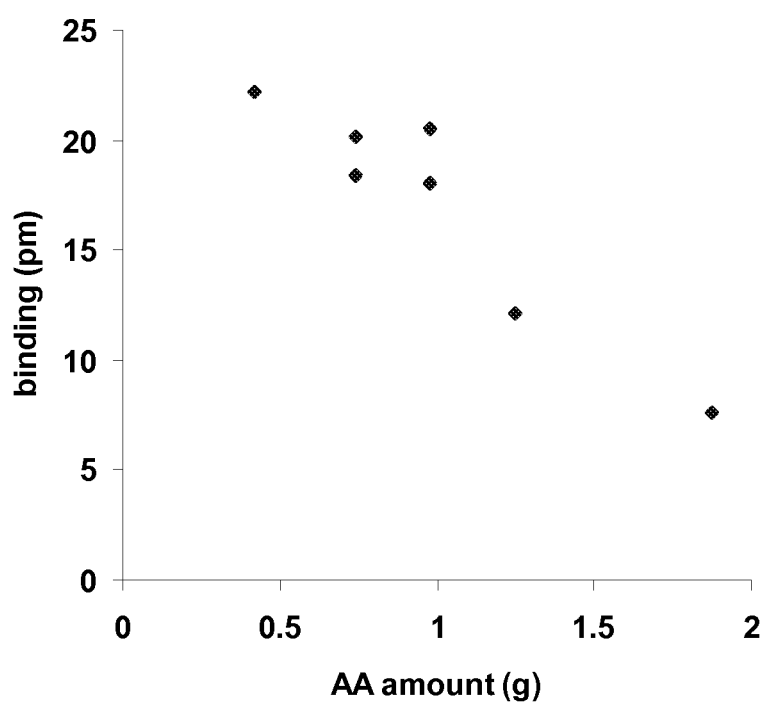
FIG. 5 shows a relationship between the amount of AA in the PAA/DMA matrix and the level of furosemide binding.

FIG. 5 is a graph showing a relationship between the amount of AA monomer in the polymer matrix and the binding values (furosemide on immobilized his-tag CAII).

Figure 6:
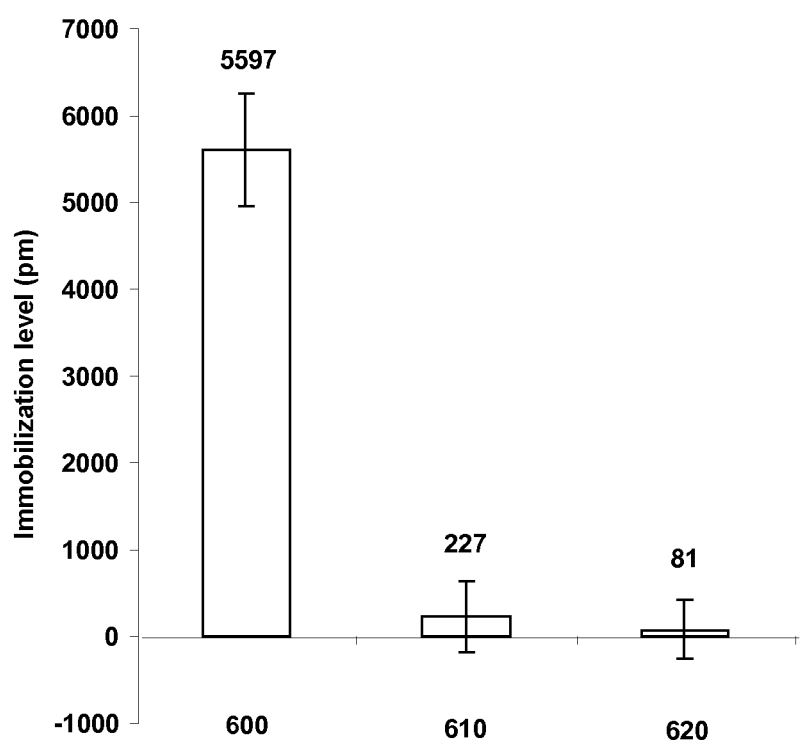
FIG. 6 show his-tag CAII immobilization on PAA-NTA surfaces with or without nickel treatment and native CAII immobilization on PAA-NTA surfaces measured with an Epic® biosensor.

FIG. 6 is a graph showing CAII or his-tag CAII immobilization level on affinity surfaces of the disclosure from Example 1; and his-tag CAII immobilization levels on affinity surfaces of the disclosure without nickel treatment. This graph demonstrates that there are no non-specific interactions.

Figure 7:
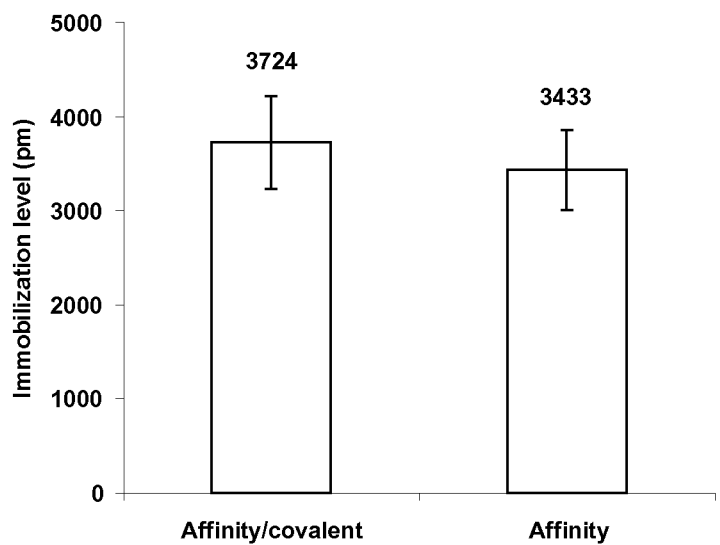
FIG. 7 shows his-tag CAII immobilization on PAA-NTA surfaces with or without affinity/covalent post treatment.

FIG. 7 is a graph showing his-tag immobilization levels on PAA-NTA made with or without affinity/covalent post treatment. The graph shows a slight improvement of immobilization level due to affinity/covalent approach on the immobilization level.

Figure 8:
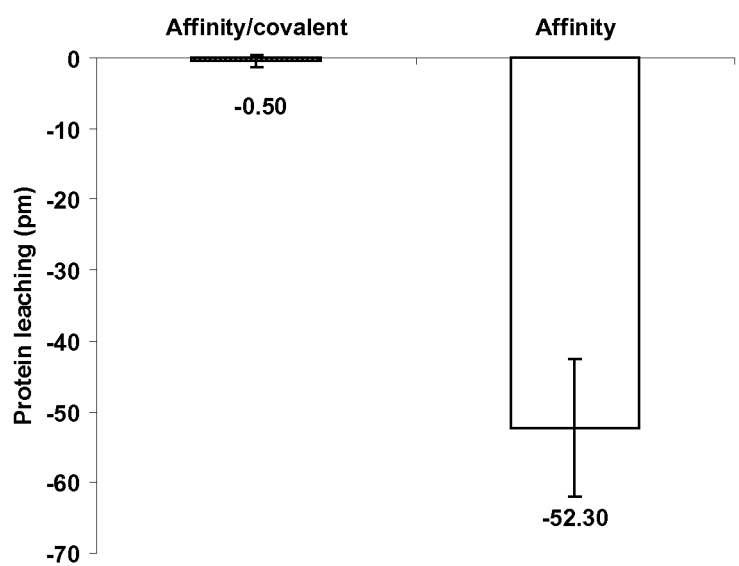
FIG. 8 shows his-tag CAII leaching from PAA-NTA after immobilization made with or without affinity/covalent post treatment.

FIG. 8 is a graph showing protein leaching from PAA-NTA surface prepared with or without affinity/covalent post treatment. This graph demonstrates the impact of affinity/covalent method on immobilized proteins as no protein leaching is observed with this treatment. At the opposite, an important protein leaching is obtained when no covalent bonds are created between proteins and the surface, which is a stopper to observe a small molecule recognition event.

Figure 9:
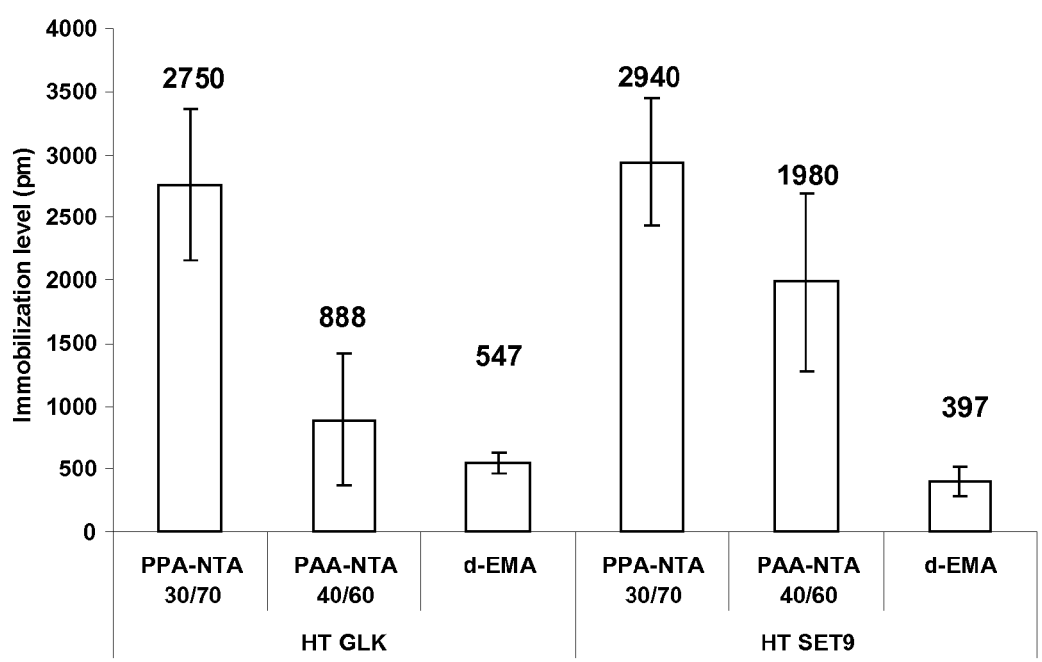
FIG. 9 shows low pI his-tag protein (GLK and SET9) immobilization measured with an Epic® biosensor on PAA-NTA surfaces and on comparative amine coupled d-EMA surfaces.

FIG. 9 is a graph showing the immobilization levels for low pI proteins (his-tag GLK and his-tag SET9: pI=4.8) on PAA-NTA chemistries (based on AA/DMA ratios 40/60 and 30/70) and on amine coupling chemistry d-EMA. This graph demonstrates the advantage of the PAA-NTA affinity chemistry of the disclosure compared to amine coupling chemistry.

EXAMPLES

The following examples serve to more fully describe the manner of using the above-described disclosure, as well as to set forth the best modes contemplated for carrying out various aspects of the disclosure. It is understood that these examples in no way limit the scope of this disclosure, but rather are presented for illustrative purposes. The working examples describe how to prepare and use the LID sensor of the disclosure which are contrasted with the comparative examples.

Example 1

Preparation of LID sensor having a "PAA-NTA" modified surface A 2 wt % methacryloxypropyltrimethoxysilane (MOPS) (from Sigma-Aldrich) aqueous solution containing acetic acid to give a pH of 3.5-4 was prepared and stirred until clear (e.g., about 15 min at room temperature). A bare Epic® insert (from Corning, Inc.)(used as received an without additional cleaning step) was contacted with the MOPS solution for 2 hours then dried argon flow and dried at 50° C. for 1 hour to ensure condensation of the silane with the insert surface. The MOPS treated insert was then cooled to RT, rinsed with DI water, then with IPA, and finally dried under argon flow.

The MOPS treated insert was contacted with an aqueous monomer mixture of acrylic acid/dimethylacrylamide (50/50) and Irgacure 184 as follows. 20 mg of Irgacure 184 (from Ciba) were weighted in a flask and 7 mL of DI water added. Then 1.5 g of acrylic acid (AA) and 1.5 g of dimethylacrylamide (DMA) was added. The flask was sealed with a septum and the solution was degassed with bubbling argon for 15 min. Next, 500 microliters of the degassed monomer mixture was deposited, such as with a liquid coater apparatus with constant dispense rate to achieve a uniform coating on the surface of the substate, dropwise, with an auto-pipettor dispensing a constant amount of monomer mixture at each of predetermined 386 well locations, and like deposition methods, onto the silane treated insert surface, and then optionally covered with a cover plate. In-situ polymerization was performed with a UV light source using a fusion lamp (bulb H, 80% power, 5 passes at the minimum belt speed). Then the cover plate was removed and the adhering gel layer was thoroughly rinsed with DI water in an ultrasonic bath to remove excess or unbound materials. The surface was finally dried under a gentle argon flow. After polymerization and cleaning, the Epic® insert was assembled with a Corning, Inc., holey well-plate using a pressure sensitive adhesive (PSA) adhesive tape. At this stage this plate was referred to as "PAA/DMAm 50/50".

The carboxylic acid groups contained within the polymer matrix on the surface were activated by treatment with a mixture of 50 mM sulfo-NHS and 200 mM EDC dissolved in water. Then, the activated copolymer was reacted with carboxymethyl lysine (CML) dissolved at 0.2M in borate buffer (pH=9.2). The impact of the pH of CML solution on subsequent his-tag CAII immobilization measured using an Epic® instrument is illustrated in FIG. 2. Residual activated esters were blocked using borate buffer (pH=9.2). Finally, nickel sulfate was added at 40 mM in water. At this stage, the microplate having the above described PAA-NTA affinity surface coating modification was ready to capture his-tag proteins.

Example 2

His-tag CAII/furosemide assay with an Epic® biosensor having PAA-NTA affinity surface modification. His-tag CAII immobilization was performed at 50 microg/mL protein in hepes+150 mM NaCl buffer at pH=7.4 on the LID sensor of Example 1. The plate was incubated overnight at 4° C. to complete immobilization. In a second step, after washing, an EDC/NHS (200 mM/50 mM) treatment was applied to the surface having the immobilized proteins, then ethanolamine was used to block remaining activated esters. This experiment was accomplished with identical conditions with several sensor surfaces have different PAA-NTA chemistries. The AA:DMA monomer ratio can be varied from, for example, about 75:25 to about 30:70 (wt/wt) or relative mole ratio (mol/mol %) or mol percent (mol %). These compositionally different PAA/DMAm matrices were further modified to PAA-NTA affinity surfaces in accord with Example 1.

After equilibration at room temperature, the PAA-NTA affinity surface plate was rinsed with PBS (using an automated workstation) and 15 microliters of PBS containing 0.1% DMSO was added to each well. Then, furosemide was added to reach a final concentration of 10 microM. Both immobilization levels and binding responses were recorded using the Epic® instrument. Immobilization levels and binding responses are shown in FIGS. 3 and 4, respectively. In addition, the impact of the amount of AA contained in the affinity surface on binding responses is given in FIG. 5.

Example 3

His-tag CAII immobilization level assay with an Epic® biosensor having PAA-NTA affinity surface modification with or without nickel treatment. The same chemical procedure of Example 1 was used to prepare a 384-well microplate coated with PAA-NTA surface modification. Addition of the nickel solution was performed only on one third of the microplate. His-tag carbonic anhydrase (His-tag CAII) was then immobilized at 50 micrograms/mL in hepes+150 mM NaCl buffers overnight on PAA-NTA surfaces with or without nickel complexation. In parallel experiments, native CAII was immobilized in hepes+salts at 50 micrograms/mL on PAA-NTA. After washing the His-tag CAII exposed microplates with PBS followed by an extensive DI water rinsing, a covalent post treatment was accomplished with EDC/NHS (200 mM/50 mM) for 30 min in water followed by an ethanolamine blocking step (0.2M in borate buffer). Then, immobilization levels were determined using the Epic® instrument and as shown in FIG. 6 for 8 His-CAII on PAA-NTA (600), CAII native on PAA-NTA (610), and 8 His-CAII on PAA-NTA without Ni ion (620). 8 His-CAII I is a carbonic anhydrase tagged with a tail bearing 8 histidines group (Octahistidine instead of the usual hexahistidine 6 His-CAII) The higher number of histidine residue improves the stability of the complex.

Example 4

His-tag CAII immobilization level on PAA-NTA surfaces with or without covalent post treatment. The procedure of Example 1 was repeated to prepare 384-well microplates having the PAA-NTA surface modification. His-tag carbonic anhydrase was then immobilized at 50 micrograms/mL in hepes+150 mM NaCl buffers for about 16 hours with PAA-NTA modified microplates. After washing with PBS and then DI water, an EDC/NHS treatment (200 mM/50 mM) was accomplished for 30 min in water followed by an ethanolamine blocking step (0.2M in borate buffer) only on one half of the microplate (corresponding to affinity/covalent interactions). The other half of the microplate was placed in soaking buffer (PBS+DMSO). Then, immobilization levels were determined using the Epic® instrument as shown in FIG. 7, and protein leaching was measured with the Epic® instrument as shown in FIG. 8 after contacting the immobilized proteins with the addition and mixing of fresh soaking buffer.

Example 5

Epic® analysis of low pI immobilization on PAA-NTA affinity surfaces. The procedure of Example 1 was repeated to prepare 384-well microplates with PAA-NTA coated surfaces (based on PAA/DMA matrixes with ratios of AA/DMA 40/60 and 30/70). Low pI his-tag proteins, such as SET9 (histone H3 methyltransferase) and GLK proteins (glucokinase) (pI=4.8 for both proteins), were immobilized at 50 micrograms/mL in hepes+salts buffer (pH=7.4) for about 16 hours. In a second step, after washing with PBS and then extensively DI water, an EDC/NHS treatment (200 mM/50 mM) was accomplished for 30 min in water followed by an ethanolamine blocking step. Immobilization levels were determined using the Epic® instrument as shown in FIG. 9. As a comparison, the same low pI proteins were also immobilized in acetate buffer (pH=5.5) at 50 micrograms/mL on amine coupled d-EMA. The comparative binding polymer, such as an amine pre-blocked poly(ethylene-alt-maleic anhydride) (d-EMA), and like polymer entities, are disclosed in commonly owned and assigned U.S. Ser. No. 11/448,486, filed Jun. 7, 2006, now US Patent Publication No. US 2007-0154348, entitled "SUPPORTS FOR ASSAYING ANALYTES AND METHODS OF MAKING AND USING THEREOF."

The disclosure has been described with reference to various specific embodiments and techniques. However, it should be understood that many variations and modifications are possible while remaining within the spirit and scope of the disclosure.

What is claimed is:

1. A biosensor article comprising:
a substrate having polymer associated with the substrate surface, the polymer comprises:
a polymer of formula (I)

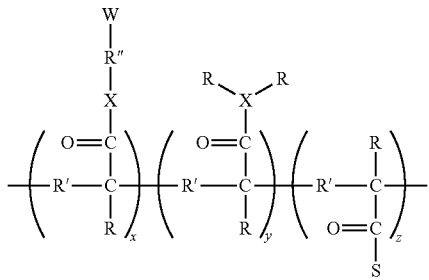

(I)

having at least one of: a metal-ion chelating group (x), an ionizable group (y), and a surface substantive group (z), where R is absent, hydrogen, or a substituted or unsubstituted, linear or branched, monovalent hydrocarbyl moiety having from 1 to 6 carbon atoms;

R' is a substituted or unsubstituted, linear or branched, divalent hydrocarbyl moiety resulting from copolymerization of an unsaturated monomer having from 1 to 18 carbon atoms;

R" is a substituted or unsubstituted, linear or branched, divalent hydrocarbyl moiety having from 1 to 20 carbon atoms;

S comprises at least one point of attachment to the substrate;

W comprises at least one metal-ion chelator moiety;

X is an —NH—, —NR—, or O; and the mole ratio of x:(y+z) groups is from about 2:8 to about 8:2.

2. The article of claim 1 further comprising the polymer having at least one metal-ion complexed with W, the at least one metal-ion comprising at least one metal-ion selected from Ni, Cu, Zn, Co, Fe, or a combination thereof.

3. The article of claim 2 further comprising a His-tagged entity associated with the at least one metal-ion complexed with W.

4. The article of claim 3 further comprising having a ligand conjugated with the associated His-tagged entity.

5. The article of claim 1 wherein

R is hydrogen, or a substituted or unsubstituted alkyl having from 1 to 4 carbon atoms;

R' is a divalent hydrocarbyl moiety having from 1 to 10 carbon atoms;

R" is a substituted or unsubstituted, divalent hydrocarbyl moiety having from 2 to 6 carbon atoms;

S is an unsaturated silane or mercapto silane substrate;

W comprises at least one iminodiacetic acid, nitrilotriacetic acid, triazacyclononane, aminoethylethanolamine, triethylenetetramine, 2-hydroxypropane-1,2,3-tricarboxylate, or a mixture thereof;

X is —NH—; and the mole ratio x:(y+z) is from about 2:1 to about 1:2.

6. The article of claim 1 wherein polymer on the substrate surface comprise a continuous layer or semi-continuous layer having a thickness of from about 20 to about 1,000 nm.

* * * * *